US00PP20994P2

(12) United States Plant Patent
Dozier, Jr. et al.

(10) Patent No.: US PP20,994 P2
(45) Date of Patent: May 11, 2010

(54) KIWI PLANT NAMED 'AU AUTHUR'

(50) Latin Name: *Actinidia deliciosa A. Chev.*
Varietal Denomination: AU Author

(75) Inventors: W. Alfred Dozier, Jr., Opelika, AL (US); Floyd M. Woods, Auburn, AL (US); Curtis J. Hansen, Opelika, AL (US); Jim Pitts, Clanton, AL (US); Robert C. Ebel, Immokalee, FL (US); Grace A. Fitzgerald, Grand Bay, AL (US); John P. Fitzgerald, legal representative, Summerdale, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 12/150,857

(22) Filed: Apr. 30, 2008

(51) Int. Cl.
*A01H 5/00* (2006.01)

(52) U.S. Cl. ..... Plt./156

(58) Field of Classification Search ..... Plt./156
See application file for complete search history.

*Primary Examiner*—June Hwu
(74) *Attorney, Agent, or Firm*—Haverstock & Owens LLP

(57) ABSTRACT

A new and distinct cultivar of the species *Actinidia deliciosa A. Chev.* is described. The parentage of this new cultivar is unknown, but it is most likely an open pollinated 'Haywood' as it was grown from seed collected from fruit purchased in a grocery store. The new cultivar is distinguished by a slightly later blooming and a bloom period that overlaps the bloom period of 'AU Fitzgerald' and 'Hayward'.

6 Drawing Sheets

RELATED APPLICATIONS

U.S. patent application Ser. No. 12/150,769, filed on Apr. 30, 2008, and entitled "Kiwi Plant Named 'AU Fitzgerald'" is incorporated by reference herein.

Latin name of the genus and species of the plant claimed: *Actinidia deliciosa A. Chev.*

Variety denomination: 'AU Authur'.

BACKGROUND OF THE INVENTION

Kiwi plants in cultivation are dioecious deciduous vines that originated in China and parts of Asia. There are over 50 species in the genus *Actinidia*. The *Actinidia deliciosa* species originated in China and parts of Asia and is known as the Chinese gooseberry. Plant material of this species was taken to New Zealand where new cultivars such as 'Hayward' were developed. Due to the appearance of the fruit of the Chinese gooseberry, it was given the name kiwi fruit in New Zealand after the native kiwi bird. The kiwi plant is dioecious thereby requiring male pollinizers in the presence of the female plants to ensure fruit production.

'Hayward' is the most commercialized female kiwi cultivar grown and marketed in the world. The 'Hayward' cultivar is produced commercially in California in the U.S. and in New Zealand, and is the kiwi fruit most often found in U.S. grocery stores. Attributes of the 'Hayward' cultivar that have led to its dominance of the kiwi market in the past are its distinctive green flesh, good flavor and long storage life. It is not known what male cultivar was used to pollinate the female flowers that produced the fruit and seed that resulted in the new cultivar. 'Mama' and 'Tomuri' are two male cultivars frequently used for pollination in 'Hayward' plantings.

Many plantings of the 'Hayward' cultivar with 'Matua' and 'Tomuri' were planted in Alabama as well as the adjoining southeastern states. These plantings were established near the coast in most cases. The vines grew vigorously but were unfruitful because the female cultivar 'Hayward' did not produce flower buds. The male plants produced flower buds and flowers. The 'Matua' cultivar bloomed earlier than 'Tomuri' in the plantings made in the coastal areas of south Alabama.

SUMMARY OF THE INVENTION

Mrs. A. A. Fitzgerald of Summerdale, Ala. purchased kiwi fruit from a local grocery store and planted some seeds from the fruit. She ended up with one female and one male plant that bloomed together, were very productive and matured a crop of quality fruit. The fruit purchased was probably from the 'Hayward' cultivar.

The present invention relates to a new and distinctive male kiwi cultivar of *A. deliciosa A. Chev.* The parentage of the new cultivar is unknown as it was grown from seed from fruit purchased from a grocery.

The new cultivar is able to be asexually reproduced as cuttings or by grafting or budding on to a seedling or cutting grown rootstock. The unique characteristics come true to form and are established and transmitted through succeeding asexual propagations. In the climate of central Alabama, vegetative bud break occurs during the last two weeks of March and the bloom period occurs during the last week of April and the first two weeks of May, depending on the climate during the season. 'Matua' generally blooms earlier than the new cultivar 'AU Authur' and during the first ¾ of the bloom period of 'AU Fitzgerald' and 'Hayward'. The bloom period of the new cultivar 'AU Authur' begins just after 'AU Fitzgerald' and 'Hayward' and overlaps the major bloom period of the female cultivars. The new cultivar 'AU Authur' peak bloom period occurs during the peak bloom period of the 'AU Fitzgerald' and 'Hayward' bloom period. 'Tomuri' blooms after 'AU Fitzgerald', 'Hayward', and the new male cultivar 'AU Authur' in most seasons.

DETAILED BOTANICAL DESCRIPTION

Figure 1:
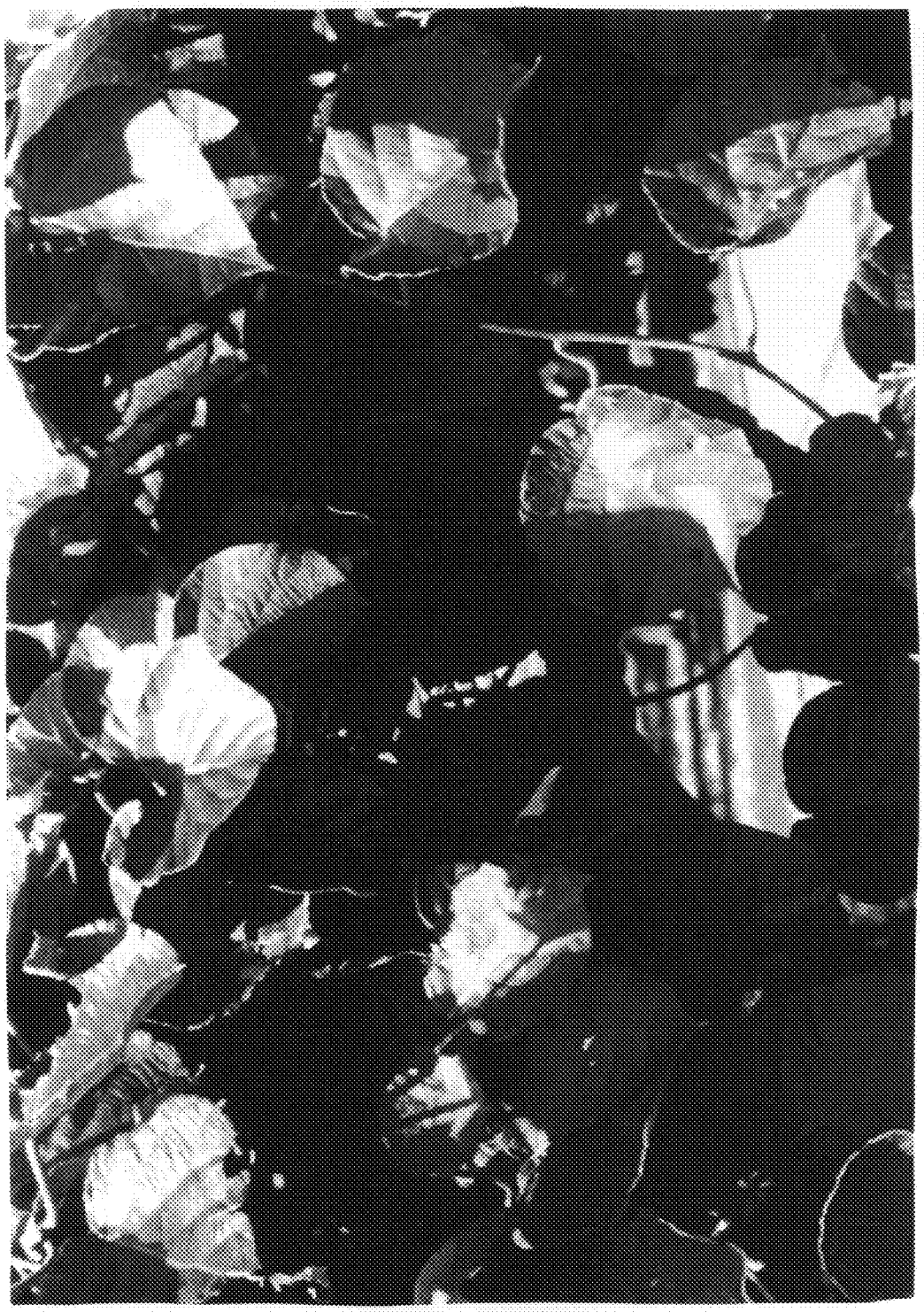
FIG. 1 is a photograph of leaves of the 'AU Authur' cultivar.
Figure 2:
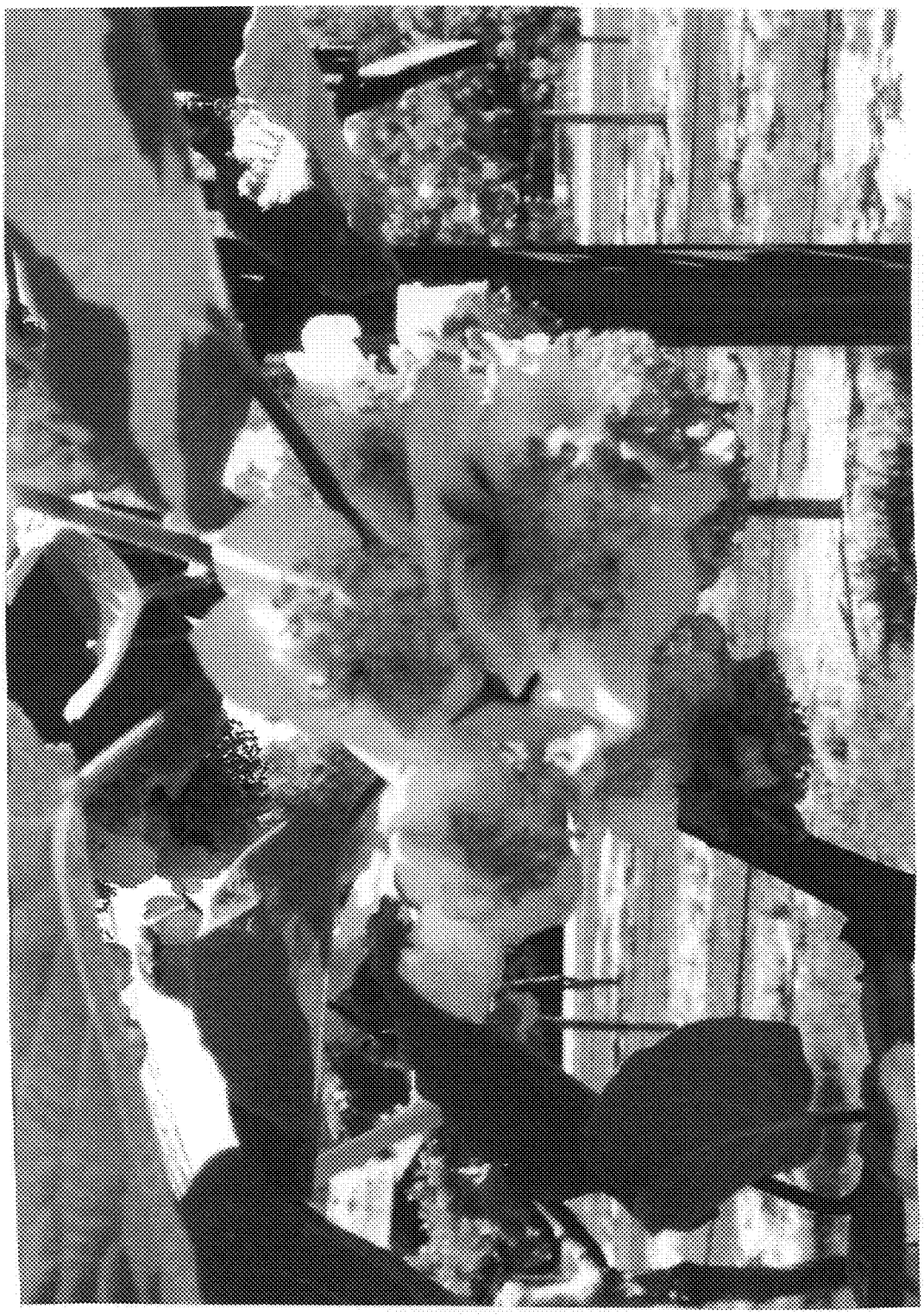
FIG. 2 is a photograph of flowers and leaves of the 'AU Authur' cultivar.
Figure 3:
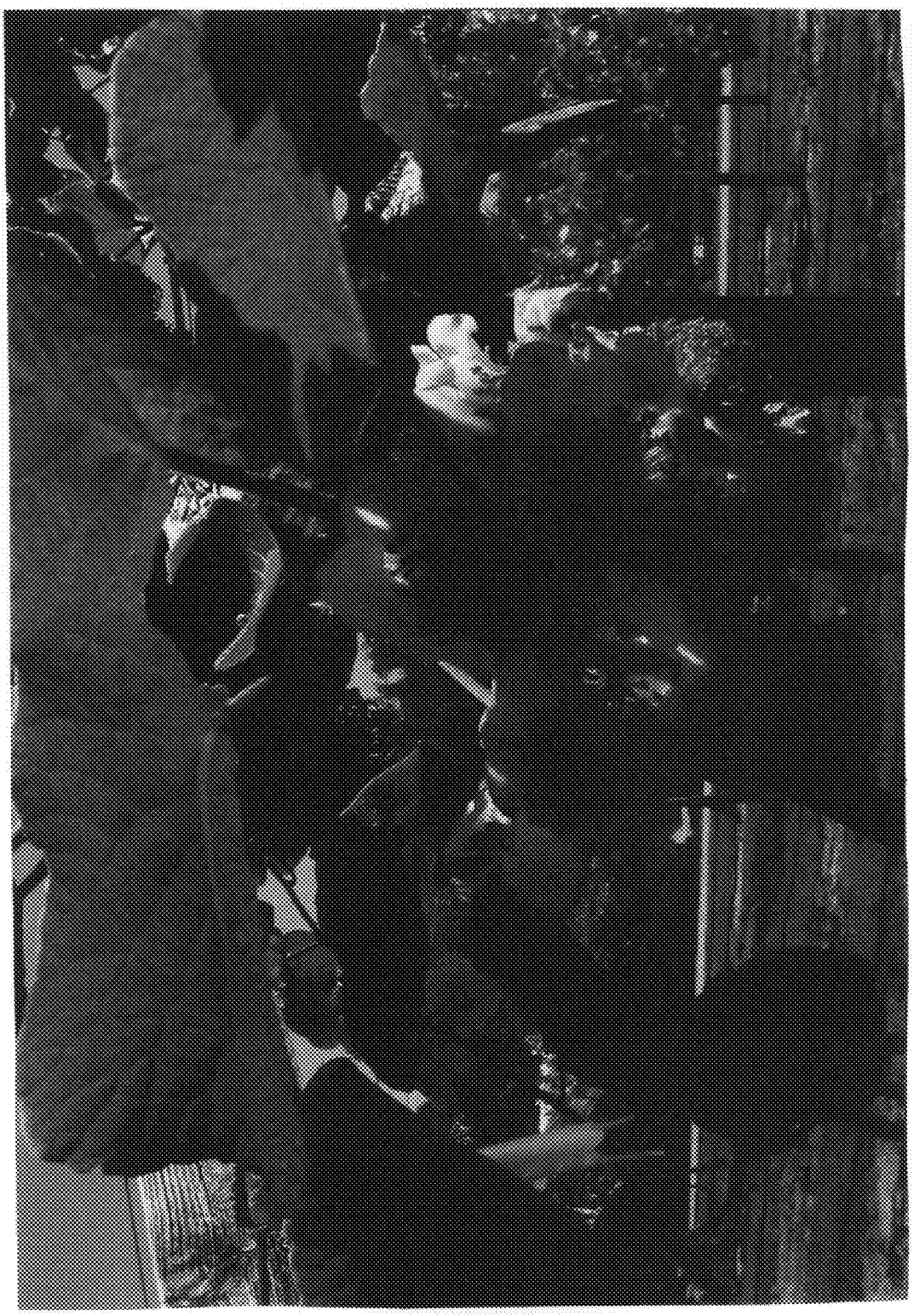
FIG. 3 is a photograph of flowers and leaves of the 'AU Authur' cultivar.
Figure 4:
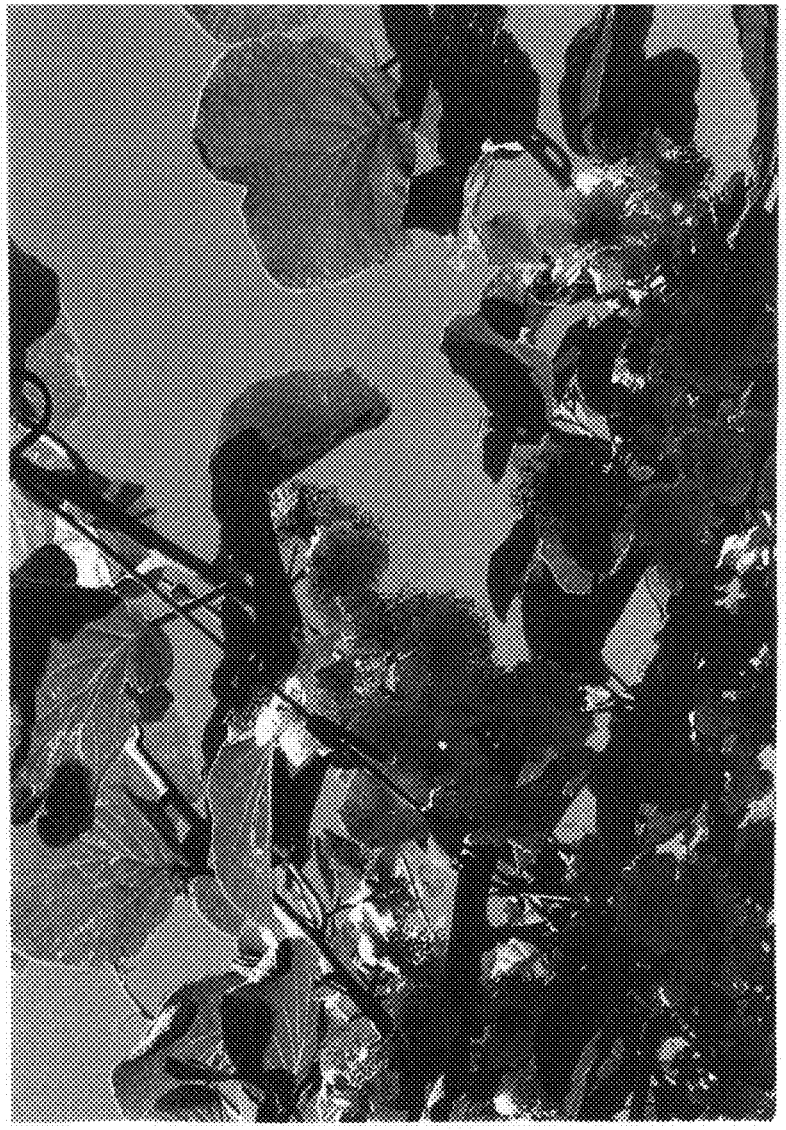
FIG. 4 is a photograph of vines, leaves and flowers of the 'AU Authur' cultivar.
Figure 5:
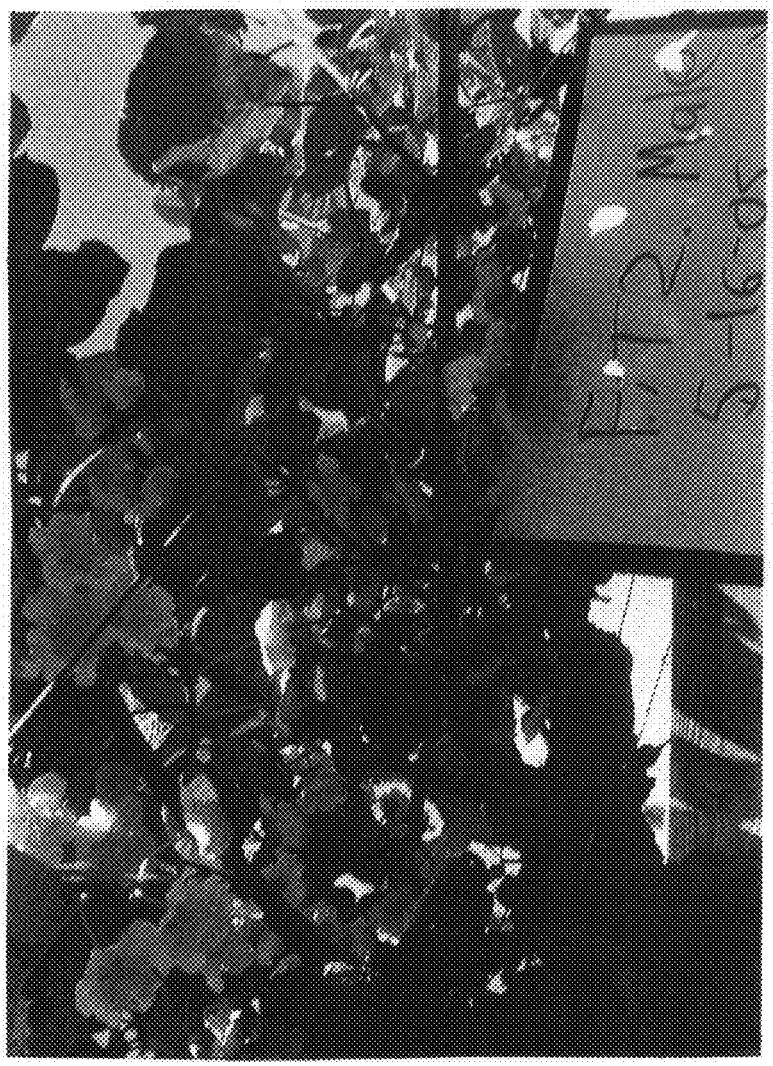
FIG. 5 is a photograph of a trunk, vines, leaves and flowers of the 'AU Authur' cultivar.
Figure 6:
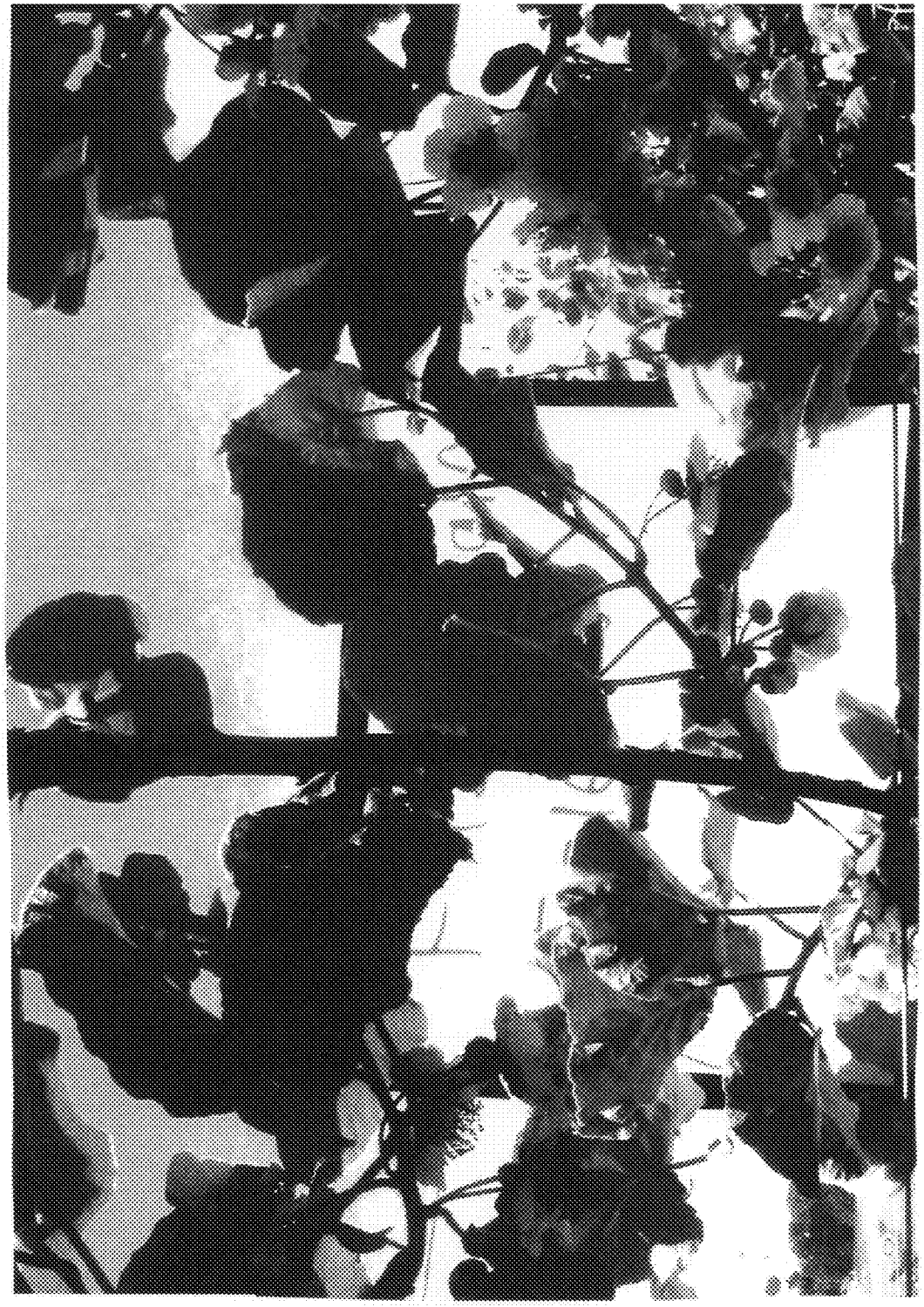
FIG. 6 is a photograph of vines, leaves and flowers of the 'AU Authur' cultivar.

The new cultivar 'AU Authur' is a male with imperfect flowers. It has 40 or more stamens per flower and vertigial pistils. Characteristics of the new cultivar in which it differs from the standard kiwi cultivar 'Matua', includes slightly later blooming and a bloom period that overlaps the bloom period of 'AU Fitzgerald' and 'Hayward'.

'AU Authur' is able to be asexually reproduced as cuttings or by grafting or budding on to a seedling or cutting grown rootstock. The new cultivar was asexually reproduced at the Chilton Area Research and Extension Center at Clanton, Ala., US. The instant plant was grafted on a rootstock named Bruno. 'AU Authur' has a vigorous growth habit similar to 'AU Fitzgerald' and 'Hayward' and blooms with these two female cultivars.

The distinctive characteristics of this new kiwi cultivar described in detail below have been observed in a replicated field experiment at the Chilton Area Research and Extension Center at Clanton, Ala., US. The plants were one year old rooted cuttings when planted. The 'Matua' and 'Tomuri' cultivars were evaluated in the same replicated field experiment and 'Matua' was used as the standard cultivar for comparison because in some years, 'Tomuri' bloomed after all other cultivars had completed the bloom period.

The table below illustrates the specific differences between the 'AU Authur' cultivar and the 'Matua' cultivar. The table utilized The Royal Horticulture Society's Colour Chart (2001).

TABLE I

Comparison of 'AU Authur' and 'Matua' cultivars.

| | 'AU Authur' | 'Matua' |
|---|---|---|
| Plant | | |
| Plant: sex expression | male (flowers imperfect) | |
| Plant: ploidy | hexaploid | |
| Plant: vigor | strong | medium |
| Young shoot: hairs | present | |
| Young shoot: density of hairs | heavy | |
| Young shoot: type of hairs | hirsute | |
| Young shoot: anthocyanin coloration of growing tip | absent | |
| Young shoot: anthocyanin coloration of leaf axil | absent | |
| Plant: average height and spread | plant is a vigorous vine trained and grown on a trellis (8'-16'). It is pruned multiple times during the season to contain the plant in its allocated space. | |
| Stem | | |
| Stem: coloration of leaf axil | weak | |

TABLE I-continued

Comparison of 'AU Authur' and 'Matua' cultivars.

| | 'AU Authur' | 'Matua' |
|---|---|---|
| Stem: diameter | medium | |
| Stem base diameter | mean 16.35 mm (range 15.5-17.1 mm) | mean 15.5 mm (range 13.75-17.74 mm) |
| Stem mid section diameter | mean 8.86 mm (range 8.57-9.4 mm) | mean 8.43 mm (range 7.55-9.74 mm) |
| Stem: dormant bud diameter | 6.62 mm (5.41-7.81 mm) | 7.12 mm (6.32-8.21 mm) |
| Stem color on upper side of shoot | light brown (N199B) | |
| Stem: character of bark | rough | smooth |
| Stem: hairs | present | present-light |
| Stem: conspicuousness of lenticels | conspicuous | |
| Stem: number of lenticels | medium 232 (174-297/sq cm) | medium 232 (174-303/sq cm) |
| Stem: color of lenticels | brownish-white | |
| Stem: size of bud support | medium-large | small-medium |
| Stem: visibility of bud (dormant canes) | almost buried | |
| Stem: number of hairs visible on bud (dormant canes) | medium | |
| Stem: leaf scar | Length (mm) 4.8 (range 4.1-6.3) Width (mm) 4.5 (range 3.9-5.2) | |
| Leaf (Mature) | | |
| Leaf shape: | orbicular to broadly cordate | orbicular to obovate, occasionally reniforme (kidney-shaped, wider than long) |
| Leaf base shape: | cordate, lobes small and touching to slightly overlapping | narrowly cordate, lobes touching to slightly overlapping |
| Leaf tip shape: | round with a broad deltoid tip | broadly obtuse to somewhat refuse with broad cuspidate at tip |
| Leaf margin: | entire | |
| Leaf adaxial surface: | light-med green (147A), glabrous except for sparse, unbranched hairs on veins | |
| Leaf abaxial surface: | light green (147B), dense, stellate pubescence everywhere except along main veins which are densely tomentose with unbranched hairs | |
| Leaf length (cm): | 18.5(15.9-23.1)[15] | 16.8(13.6-20.5)[15] |
| Leaf width (cm): | 15.1(12.5-17.9)[15] | 14.1(12.0-20.8)[15] |
| Leaf ratio (l/w): | 1.2(1.1-1.5)[15] | 1.2(0.9-1.4)[15] |
| Leaf petiole length (cm): | 5.6(3.9-9.9)[15] | 4.2(3.3-6.3)[15] |
| Leaf 1° vein organization: | pinnate; veins terminating as small extended points or mucros at leaf margins | |
| Leaf 2° vein organization: | ±parallel | |
| Leaf puckering: | weak | moderate |
| Leaf variegation: | none | |
| Leaf spines on lower leaf surface: | none | |
| Petiole: | N199B | |
| Pedicel: | 149D | |
| Flower | | |
| Inflorescence#: | mean 2.6 (range 1-4) [15] | mean 2.4 (range 1-4) [28] |

TABLE I-continued

Comparison of 'AU Authur' and 'Matua' cultivars.

| | 'AU Authur' | 'Matua' |
|---|---|---|
| 1° Pedicel length (cm): | 4.0(2.0-6.2)[12] | 2.6(1.4-3.3)[17] |
| 2° Pedicel length (cm): | 1.6(0.9-2.8)[16] | 0.9(0.6-1.5)[18] |
| Pedicel pubescence: | minutely, densely tomentose, unbranched | |
| Sepal#: | 5.4(3-7)[11] | 5.3(4-7)[17] |
| Sepal color: | 152D | rusty greenish |
| Sepal pubescence: | minutely, densely tomentose, unbranched creamy white | |
| Flower color: | 10D | |
| Flower width (cm): | 5.4(5.1-5.8)[10] | 3.8(3.6-4.1)[12] |
| Petal orientation: | overlapping: sides reflexed | |
| Petal#: | 6.8(5-8) [11] | 6.0 (5-7) [14] |
| Petal length (cm): | 2.4(2.2-3.0)[20] | 1.9(1.6-2.1)[19] |
| Petal width (cm): | 2.1(1.8-2.5)[20] | 1.5(1.2-1.8)[19] |
| Petal ratio (l/w): | 1.2(0.9-1.4)[20] | 1.3(0.9-1.5)[19] |
| Petal arrangement: | overlapping | |

TABLE I-continued

Comparison of 'AU Authur' and 'Matua' cultivars.

| | 'AU Authur' | 'Matua' |
|---|---|---|
| Style#: | average - 24<br>range (20-28) | |
| Stamen#: | average - 153<br>range (142-168) | |
| Anther length (mm): | 2.0-3.0 | |
| Chilling requirement hours: | <800 | |
| Filament: | 10C | |
| Anther: | 21B | |

What is claimed is:

1. A new and distinct variety of *Actinidia deliciosa* plant named 'AU Authur', substantially as described and illustrated herein.

* * * * *